United States Patent
Widl et al.

(10) Patent No.: US 10,502,341 B2
(45) Date of Patent: Dec. 10, 2019

(54) OPTICAL MICROPHONE TO DIAGNOSE ACTUATORS

(71) Applicant: SAMSON AKTIENGESELLSCHAFT, Frankfurt (DE)

(72) Inventors: Andreas Widl, Munich (DE); Gerhard Widl, Feldafing (DE); Stefan Unland, Offenbach (DE); Uwe Schwab, Osthofen (DE)

(73) Assignee: SAMSON AKTIENGESELLSCHAFT, Frankfurt (DE)

( * ) Notice: Subject to any disclaimer, the term of this patent is extended or adjusted under 35 U.S.C. 154(b) by 0 days.

(21) Appl. No.: 15/874,260

(22) Filed: Jan. 18, 2018

(65) Prior Publication Data
US 2018/0202577 A1  Jul. 19, 2018

(30) Foreign Application Priority Data
Jan. 18, 2017 (DE) .......... 10 2017 100 956

(51) Int. Cl.
*F16K 37/00* (2006.01)
*G01N 29/036* (2006.01)
(Continued)

(52) U.S. Cl.
CPC ........ *F16K 37/0083* (2013.01); *F16K 37/005* (2013.01); *F16K 37/0041* (2013.01);
(Continued)

(58) Field of Classification Search
CPC ............ F16K 37/0083; F16K 37/0041; F16K 37/005; F16K 37/0058
(Continued)

(56) References Cited

U.S. PATENT DOCUMENTS 6,530,277 B2  3/2003  Kumpfmueller
6,637,267 B2  10/2003  Fiebelkorn et al.
(Continued)

FOREIGN PATENT DOCUMENTS

DE          19924377 B4   12/2004
DE    10 2005017054 A1    3/2006
(Continued)

OTHER PUBLICATIONS

German Office Action dated Oct. 13, 2017 for German application No. 10 2017 100 956.6.
(Continued)

*Primary Examiner* — Allen T Cao
(74) *Attorney, Agent, or Firm* — Schiff Hardin LLP

(57) ABSTRACT

A diagnostic system and method to function-monitor an actuator to affect a process medium stream of a process engineering plant can include an optical microphone allocated to the actuator and a diagnostic electronics. The optical microphone can be configured to measure an acoustic, actuator-specific operating signal, as leakage sound and cavitation sound, based on electromagnetic radiation that is affected by the acoustic, actuator-specific operating signal, and generate an electrical measuring signal based on the measured acoustic, actuator-specific operating signal. The diagnostic electronics can be configured to receive and store, process, and/or transmit the electrical measuring signal.

16 Claims, 2 Drawing Sheets

Figure 1:
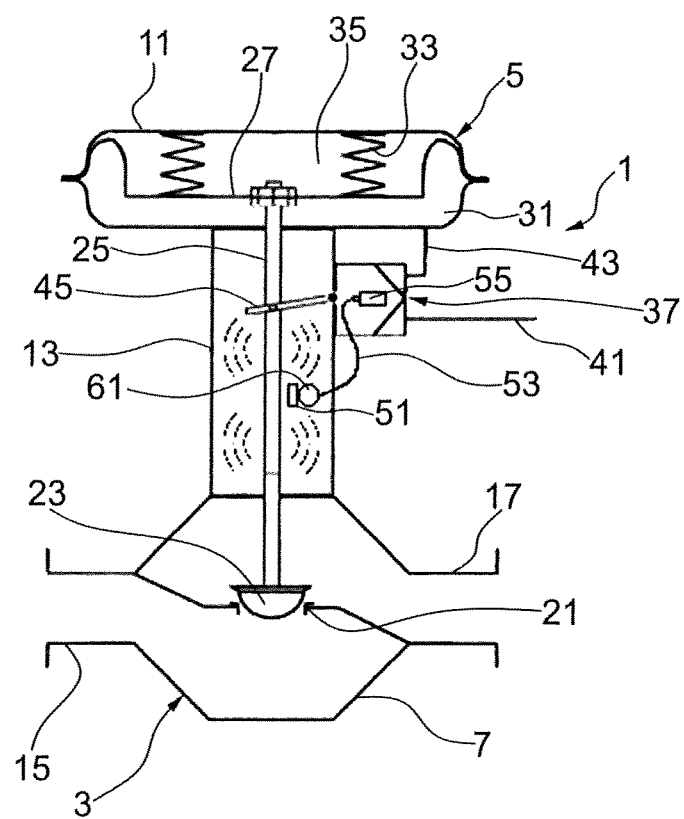

(51) Int. Cl.
*H04R 29/00* (2006.01)
*G01H 9/00* (2006.01)
*G01M 3/02* (2006.01)
*G01M 3/24* (2006.01)
*G01M 3/38* (2006.01)
*H04R 1/02* (2006.01)
*H04R 23/00* (2006.01)
*E21B 47/10* (2012.01)

(52) U.S. Cl.
CPC ........... *F16K 37/0058* (2013.01); *G01H 9/00* (2013.01); *G01M 3/025* (2013.01); *G01M 3/24* (2013.01); *G01M 3/38* (2013.01); *G01N 29/036* (2013.01); *H04R 1/028* (2013.01); *H04R 23/008* (2013.01); *H04R 29/004* (2013.01); *E21B 47/101* (2013.01)

(58) Field of Classification Search
USPC .................................................. 367/197–199
See application file for complete search history.

(56) References Cited

U.S. PATENT DOCUMENTS

| | | | |
|---|---|---|---|
| 8,122,905 B2 | 2/2012 | Pape et al. | |
| 8,429,951 B2 | 4/2013 | Puttmer | |
| 2007/0067678 A1* | 3/2007 | Hosek | G05B 23/0235 714/25 |
| 2008/0141775 A1 | 6/2008 | Pape et al. | |
| 2011/0123199 A1* | 5/2011 | Hashimoto | G01H 9/004 398/134 |
| 2013/0308957 A1* | 11/2013 | Iwamoto | H04R 23/008 398/133 |
| 2014/0005958 A1 | 1/2014 | Baliga | |
| 2015/0059886 A1 | 3/2015 | Anderson | |
| 2015/0355080 A1* | 12/2015 | Mitchell | G01N 21/3504 356/73 |
| 2016/0191659 A1* | 6/2016 | Farrell | H04L 67/32 709/219 |
| 2017/0076451 A1* | 3/2017 | Pauly | G16H 50/20 |
| 2017/0091009 A1* | 3/2017 | Bhattacharyya | G06F 11/079 |
| 2017/0234837 A1* | 8/2017 | Hall | B06B 3/00 73/602 |

FOREIGN PATENT DOCUMENTS

| | | |
|---|---|---|
| DE | 10 2006013345 A1 | 10/2007 |
| DE | 102006059938 B3 | 3/2008 |
| DE | 10 2006055747 A1 | 5/2008 |
| EP | 0637713 A1 | 2/1995 |
| EP | 1216375 B2 | 3/2006 |
| EP | 2191182 B1 | 4/2013 |
| JP | S6018100 A | 1/1985 |
| WO | 02077733 A1 | 10/2002 |
| WO | 2011083760 A1 | 7/2011 |
| WO | 2015031416 A1 | 3/2015 |

OTHER PUBLICATIONS

EP Search Report; dated Jun. 14, 2018 for EP patent application No. 18151759.0 (includes partial English translation).
"Sennheiser Introduces Optical Microphone for Industrial & Medical Applications", https://www.prosoundweb.com, EH Publishing (2018).

* cited by examiner

OPTICAL MICROPHONE TO DIAGNOSE ACTUATORS

CROSS REFERENCE TO RELATED APPLICATIONS

This patent application claims priority to German Patent Application No. 102017100956.6, filed Jan. 18, 2017, which is incorporated herein by reference in its entirety.

BACKGROUND

Actuators, as control valves, affecting, in particular controlling by open-loop control and/or close-loop control, the process medium stream of the process engineering plant can take on critical operating conditions. In case of control valves, these critical operating conditions are for example leakage or cavitation which are accompanied by a characteristic sound emission. Sound emissions of the actuator can be acoustically recorded and evaluated. An early detection of actuator damages has to be achieved to avoid a complete failure of the actuator or an interruption of the plant operation as for example due to acute maintenance or repair works on the process engineering plant.

A diagnostic system for control valves and close valves of a process engineering plant is described in EP 0 637 713 A1. The diagnostic system uses an electric processor of a positioner that is connected with a structure-borne sound sensor that monitors an upper valve part and generates measured values for determining cavitation. In case of an impermissible deviation of the measured sound values from reference measured values being recorded before during proper operation of the positioner, an alarm signal is emitted. Due to the direct arrangement of the structure-borne sound sensor at the upper valve part, the diagnostic system is susceptible for false alarms since the source of the sound can only be identified with an increased diagnostic effort.

A diagnostic system for a positioner of a control valve of a process engineering plant is described in DE 199 24 377 B4. In this document, a structure-borne sound sensor is mounted directly at the outside of the control valve housing. A structure borne sound spectrum is recorded when the control valve is slightly open and compared during operation when the control valve is closed. After comparison of both measured values a conclusion regarding the tightness or the leakage of the control valve can be made. Also with this diagnostic system a high reliability is not to be assumed.

In EP 1 216 375 B2, it is proposed to mount a sound sensor to the yoke, i.e. to a connection flange between the actuating drive housing and the control valve housing, to a flange between the control valve housing and the plant conduit, or to the valve rod itself. Mounting the sound sensor to the valve rod bears the advantage that especially high-frequency sound signal parts of adjacent components in the process engineering plant which are for example transmitted through the conduit are muffled and attenuated. The structure-borne sound of the control valve to be monitored that characterizes the operation can be scanned directly via the closing body and thus via the valve rod. It is further proposed to use a piezoelectric transducer element for the sound sensor that is designed insensitive in the area of low frequency operating noise and sensitive in the area of higher-frequency operating noise. This is based on the knowledge that different operating conditions, in particular operating error types, show characteristic derivations from specific frequency bands. The known diagnostic system suffers from a complex signal evaluation and a low reproducibility.

A diagnostic device for a field device in the industrial environment of a procedure engineering plant is described in WO 02/077733 A1. The field device is connected via a data path with a central controller and comprises an acoustic data recording device in form of a microphone. In case of derivation of the noise information to stored data of a central controller the functionality of the field device can be verified. This diagnostic device has the drawback of low measurement accuracy.

DE 10 2006 055 747 A1 describes a diagnostic system for an actuator that is operated via a pneumatic actuating drive which is controlled by a positioner. For checking the correct functionality of the control valve, it is known that specific acoustic signals are emitted during the intended use. These should be recorded in the pneumatic actuating drive, from which conclusions about the state of the control valve should be made. This is based on the knowledge that acoustic signals are transmitted to the diaphragm of the pneumatic actuating drive, which acoustic signals are amplified by the large diaphragm and passed to the air pressure medium. As acoustic sensor a pressure sensor is used. The diagnostic system also suffers from a low reliability and a high diagnostic effort to filter out the essential signals from the nonessential signals in view of the assessment of the functionality of the control valve.

A method for the diagnosis of a pneumatically operated control valve is described in DE 10 2006 059 938 B3. A positioner controls the pneumatic auxiliary energy which is fed to an actuating drive. The positioner has a nozzle-flapper arrangement which is additionally used as sensor. Such a diagnostic system is temperature-dependent and thus rather unsuitable for the use in the process engineering plant.

EP 2 191 182 B1 describes a structure-borne sound sensor which is integrated in a fastening screw which mounts the positioner to the field device. For identification of a leakage at the actuating drive, the pressure of the process fluid is measured at the inlet side and compared with a reference pressure. The diagnostic system triggers an alarm when the measured structure-borne sound level exceeds a reference value and at the same time a pressure measured value is smaller than the reference pressure value. Precise statements about a leakage or cavitation cannot be obtained with the known system.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 2:
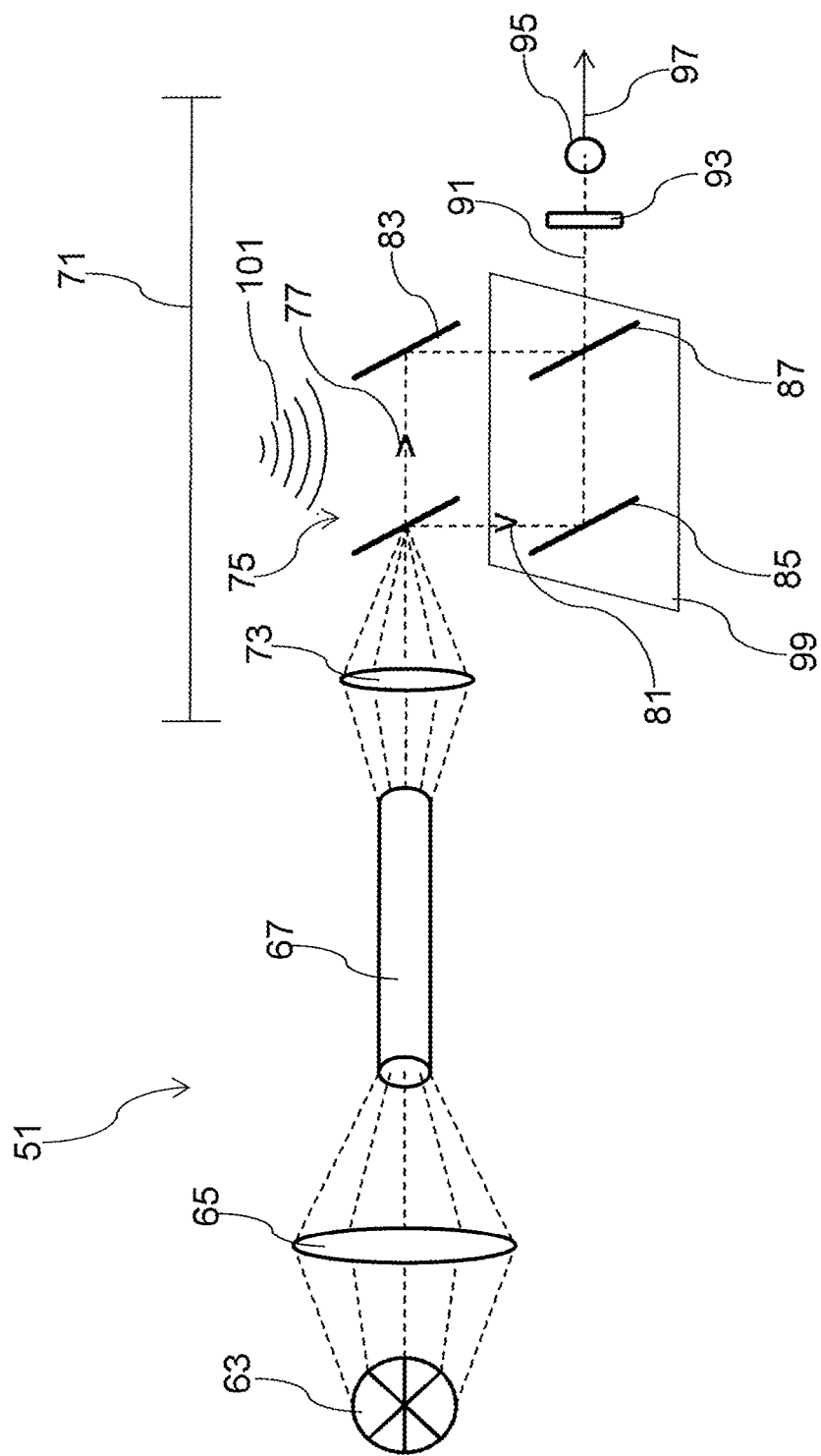

FIG. 1 illustrates a schematic diagram of an actuator with an diagnostic system according to an exemplary embodiment of the present disclosure; and FIG. 2 illustrates a functional principle diagram of an optical microphone the diagnostic system according to an exemplary embodiment of the present disclosure.

The exemplary embodiments of the present disclosure will be described with reference to the accompanying drawings.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

The disclosure relates to a diagnostic system to function-monitor an actuator of a process engineering plant, such as a chemical plant, a food processing plant, a power plant, or the like. In an exemplary embodiment, an actuator includes at least one control valve, such as an emergency closing control valve or a closed loop control valve, through which a medium stream, in particular a fluid stream, of the process engineering plant can be controlled and adjusted. The actuator can also be run by auxiliary power, as pneumatic, wherein in particular the actuating drive can be operated through an in particular electro-pneumatic positioner. Further, the disclosure relates to the actuator as such that includes the diagnostic system. The disclosure also relates to a field device of a process engineering plant that can be used to close-loop control the process medium stream. The field device is an actuator being integrated into the process engineering plant that can for example beside a control valve include an actuating drive and electronics that control the actuating drive, wherein for example also a pump can be connected in combination. The process medium stream can be a process fluid stream that underlies explosion protection when processing in large-scale plants. The diagnostic system can match the requirements of the security technology for avoiding explosions, wherein ignition protection classes according to norms, as IEC, EN, ATEX, or NEC are defined.

In one or more exemplary embodiments, a diagnostic system is provided, which is configured to function-monitor an actuator of a process engineering plant with which early detection of actuator damages, as leakage and cavitation, can be achieved with high reliability and as precise as possible.

In an exemplary embodiment, a diagnostic system for function-monitoring an actuator, as a control valve, can be configured to affect a process medium stream of a process engineering plant. The plant can include, for example, a chemical plant, a food processing plant, a power plant, or the like. In an exemplary embodiment, the actuator can be configured to set an explosion-endangered process medium stream. The diagnostic system as well as the actuator are suitable to be used in the EX-area. For the actuator comprising the diagnostic system of one or more embodiments, ignition protection can be accounted for. Pneumatic can be used as auxiliary drive energy to avoid high electrical voltages and current flows. For diagnosis and sensors, a small electrical power, in particular of a few watts, can be used.

In an exemplary embodiment, the diagnostic system includes an optical microphone that is orientated to a structural element, as an inner organ or the outer side, of the actuator. The optical microphone can be configured to measure an acoustic, actuator-specific operating signal or operating noise, as leakage sound or cavitation sound, by electromagnetic radiation (e.g. light), that is affected by the acoustic, actuator-specific operating signal. Thereby, the optical microphone uses the changes of the electromagnetic radiation at a microphone-specific orientation point (e.g. changes that result due to sound, in particular sound pressure waves) to measure the acoustic, actuator-specific operating signal or operating noise, as leakage sound or cavitation sound. The optical microphone can generate an electrical measuring signal that depends on the acoustic operating signal. Furthermore, the diagnostic system according to an exemplary embodiment has an diagnostic electronics that receives the electrical measuring signal of the optical microphone and particularly subsequently stores, processes and/or transmits said signal, in particular to actuator-specific electronics, such as a microcomputer for example of a positioner, or to a control room of the process engineering plant being connected with the actuator.

The diagnostic system according to an exemplary embodiment can use an optical microphone which either uses existing electromagnetic radiation, such as the visible part (e.g. 380 nm to 780 nm, ambient light), or has an artificial, microphone-own light source which can, for example, be realized as a laser diode. In an exemplary embodiment, the light source cooperates with a measuring head that can for example be formed as interferometric mirror. The measuring head may be movably mounted relative to the light source. The light source may additionally or alternatively be movably mounted. In an exemplary embodiment, both light sources are arranged stationary to each other. In an exemplary embodiment, the measuring head and the light source of the optical microphone are flexibly coupled with each other by, for example, a deformable optical fiber such that a relative movement between measuring head and light source is permitted without impairing the optical light-wave-guide between measuring head and light source. In this way, when using a sensitive laser diode, the diode can be arranged in a protected area, for example in a housing, separated from the measuring head and/or the orientation point to be not exposed to harsh environment conditions at or in the actuator.

In an exemplary embodiment, the sound pressure generated by the acoustic, actuator-specific operating signal (e.g. its change) is optically detected via the change of the refractive index in the air which is caused by sound waves. The acoustic, actuator-specific operating signals are typical operating noises which are emitted by the actuator with increased intensity at certain locations of the actuator. These locations of increased noise intensity are often difficult to access for detection, but can be scanned with the optical microphone. For example, the leakage sound or cavitation sound can (e.g. in the vicinity of the closer of the actuator) be recorded with high intensity. The sensor can be arranged in the process medium which can be achieved using an optical microphone. For the diagnosis, reference values, such as empirical values, for operating noises can be stored, or can as part of an initialisation process, be specifically recorded for the respective actuator to individually have a specific noise fingerprint as comparison reference value for each actuator. A leakage sound can, for example, be actuator-specific recorded by opening the intact actuator in accordance with a conventional leakage wear passage by what typical stream noises are set which are actuator-specific stored.

In an exemplary embodiment, a precise conversion of the acoustic operating signal, or of the operating noise into electrical measuring signals is achieved by the optical microphone. The optical microphone can be configured to detect the variability (e.g. changes) of the ambient light due to the sound pressure fluctuations, and/or detect the change in the light speed of a light beam of a microphone-own light source, such as a laser beam, which passes the sound field. The change in the light speed is proportional to the sound pressure. It is, for example, possible to use an interference arrangement by comparing changes in the light speed in a sound-free air field with those of the sound field being permeated with operating noise. Therefore, the optical microphone can have, for example, two laser beam sources which travel the same distance. In this example, the one beam traversing field is unaffected by the acoustic, actuator-specific operating signal, while the sound field is penetrated by the operating signal. In an exemplary embodiment, a detector is provided that is configured to detect the interfering laser beams. The detector can be configured to output the measured interference as an electrical measuring signal. In an exemplary embodiment, the detector includes processor circuitry that is configured to perform one or more operations and/or functions of the detector, such as detecting the interfering laser beams and generating the electrical measuring signal based on the measured interference.

In an exemplary embodiment, the optical microphone includes a first interferometer and a second interferometer, each of which can receive light from one and the same light source. By using multiple interferometers, a very meaningful spatial resolution of the sound field is achieved. Each interferometer can have a beam splitter for itself which sends the light beam or laser beam in two different, but equally long ways. The one partial beam is exposed to the sound field, the over is acoustically isolated. Both partial beams are, after they have usually been reflected several times by mirrors, again brought together and interfere with each other. In an exemplary embodiment, the respective interferometer is a Fabry-Perot-Interferometer, but is not limited thereto.

With the diagnostic system, increased reliability in the early detection of wear damages, in particular leakage and cavitation, can be achieved in the fields of procedural use of actuators, in particular control valves, of process engineering plants. It has been found that the contactless measurement of acoustic operating noises being specific for certain operating states of the actuator can precisely be detected without structural contacting. Surprisingly, it has also been found that just the use of an optical microphone which detects sound waves by the change of the refractive index of a gas medium being permeated with sound waves, as air, achieves notably precise measurements for high frequencies which are especially important in the determination of cavitation and precise leakage quantities. The diagnostic system is especially advantageous because it can be designed to be robust and compact. It allows making measurements in places which were according to the state of the art previously not possible. In particular, sound measurements can be made directly in the process medium itself, for example in the vicinity of the closing body of the control valve. It is also possible to carry out measurements on pneumatically exposed drive diaphragms, in particular to check the operational capability of a pneumatic actuating drive with diaphragm structure. In contrast to most of the known diagnostic systems, the own influence of the arrangement of the diagnostic system itself on the sound field to be detected is small. The sound field is hardly affected by the prevailing or generated microphone-own light. Furthermore an electromagnetic disturbance of the sound field can be excluded with the diagnostic system.

The optical measurement method can be used in the sound field of air or other gases/fluids/liquids. Gaseous media in which the light speed changes due to sound pressure waves in the medium are generally suitable.

In an exemplary embodiment, to generate the electrical measuring signal that is dependent on the acoustic, actuator-specific operating signal, the optical microphone can include a corresponding transducer. In an exemplary embodiment, the transducer includes one or more interferometer with a stationary or movable mirror. For example, one or more radiation detectors can be provided which are configured to detect the electromagnetic radiation being influenced by the sound waves, and to convert the detected, influenced electromagnetic radiation into the magnetic measuring signal.

In an exemplary embodiment, diagnostic electronics of the diagnostic system receives the electrical measuring signal. In an exemplary embodiment, the diagnostic electronics is a memory, such as ROM or RAM, and/or as microcomputer. In an exemplary embodiment, the diagnostic electronics can store the electrical measuring signal. The memory may be configured to operate without a permanently fed electric energy so as to receive the stored signal. In an exemplary embodiment, the diagnostic electronics can configured to evaluate the electrical measuring signal, including with regard to a reference value. If the reference value is exceeded, the diagnostic electronics can be configured to output an alarm signal, acoustically and/or optically. In an exemplary embodiment, the diagnostic electronics can be configured to influence a closed-loop control of a positioner of the actuator via the electrical measuring signal. For example, the diagnostic electronics can be configured to forward the electrical measuring signal to a further electronic component, such as the positioner, a control room of the actuator, a transmitting device, a display device of the actuator, etc. In an exemplary embodiment, the diagnostic electronics includes processor circuitry that is configured to perform one or more operations and/or functions of the diagnostic electronics, such as receiving and storing the electrical measuring signal, process and/or evaluate the received signal, output an alarm signal, influence the closed-loop control of the positioner, and/or forward the electrical measuring signal.

In an exemplary embodiment, the optical microphone is designed without diaphragm and therefore requires no movable components. In this example, an extremely precise identification of the acoustic, actuator-specific operating signal is achieved. In an exemplary embodiment, the optical microphone is configured to record sound pressure optically via the recording of the change of the refractive index of the air in the course of the sound waves of the acoustic, actuator specific operating signal.

In an exemplary embodiment, the optical microphone is arranged in the inside of a housing of the actuator, such as the valve housing of the control valve. In this example, the inside of the housing is adapted to allow a process medium to flow therethrough. The optical microphone can be orientated to a valve closer, a valve seat, and/or a valve rod of the control valve. Alternatively or additionally, a further optical microphone can be arranged in a conduit of the process engineering plant adjacent to the actuator that leads the process medium. The optical microphone can be orientated to the inside of the housing of the actuator. Alternatively or additionally the optical microphone can be arranged in a pneumatic conduit of a pneumatic actuating drive system of the actuator. For example, the optical microphone can be orientated to a magnet valve of a positioner of the actuator. Alternatively or additionally, the optical microphone can be arranged in a pneumatic working chamber of a pneumatic actuating drive of the actuator. The optical microphone can be orientated to a diaphragm or a bellow of the actuator that separates two working chambers of the actuator from each other. Alternatively or additionally, the optical microphone can be arranged outside of the actuator (e.g. of the actuator housing) at, for example, the yoke or lantern connecting the control valve with the actuating drive, a connecting flange (e.g. of an actuating drive) and the control valve (e.g. of a housing of the control valve) on the drive rod of the control valve itself near the positioner. In the case of an arrangement in a conduit, the optical microphone can be arranged at a stream divider on which specific operating noises can be expected. A further alternative or additional positioning of an optical microphone can be realized on the connecting threaded bolt which for example acts as a sound bridge between the valve housing and the yoke. In an exemplary embodiment, the optical microphone is arranged in the stream of the process fluid itself.

In an exemplary embodiment, the optical microphone is formed by an arrangement of at least two, optical sub-microphones. In an exemplary embodiment, exactly two or three optical sub-microphones are used, but is not limited thereto. The sub-microphone(s) can be configured as described in one or more embodiments herein. In an exemplary embodiment, the sub-microphone(s) (e.g. each microphone) are configured to generate sound-wave-specific electrical measuring signals. In an exemplary embodiment, the arrangement is carried out in such a way, the at least two sub-microphones are arranged with respect to each other such that a sound field of the acoustic, actuator-specific operating signal can be determined and displayed in a multi-dimensional manner via the measuring signals respectively generated by the microphone. In an exemplary embodiment, the arrangement of at least two sub-microphones can, for example, be coupled with the diagnostic electronics in a signal transmission manner (e.g. communicatively coupled). The diagnostic electronics can process, store, and/or transmit the at least two measuring signals. In an exemplary embodiment, the diagnostic electronics is configured to perform a three-dimensional resolution of the sound field via the transmitted measuring signal of three optical sub-microphones. In an exemplary embodiment, the diagnostic electronics can perform the evaluation of the measuring signals of the arrangement in such a way that the diagnostic electronics localizes the sound source, in particular of the leakage or the cavitation, and/or determines the sound velocity.

In an exemplary embodiment, a multi-dimensional resolution of the sound field can also be achieved with a single microphone. In this example, the microphone (at least in part) can be movable with respect to the sound field to be detected to take several "perspectives" for the optical detection of the sound field. In this example, it is not necessary to use a variety of optical microphones, but rather a plurality of measuring heads (e.g. interferometric mirrors) can be supplied with a single laser diode whose light is coupled into a plurality of optical fibers.

In an exemplary embodiment, the diagnostic system includes an adjuster or displacer configured to move at least one part of the optical microphone, such as its measuring head, for example of an interferometric mirror or light source, relative to a spatially defined sound field at the actuator. In an exemplary embodiment, the displacement path is predefined (e.g. translationally determined). With the adjuster/displacer, a multi-dimensional resolution of the sound field with a single optical microphone can be obtained. In an exemplary embodiment, the adjuster/displacer includes a drive (e.g. electric drive) which can displace the at least one part of the optical microphone. The drive can, for example, include a piezoelectric material and/or is supplied with energy (e.g. electrical energy) which is taken from, for example, the process medium stream or an auxiliary energy source, such as a pneumatic pressure source. In this case, an autarkic energy supply of the diagnostic system can be achieved. The energy taken from the environment, the process stream, and/or the auxiliary energy can also be used to operate the light source (e.g. laser diode) in addition to operating the displacer/adjuster, after conversion into electrical energy via a respectively dimensioned generator. In embodiments where the optical microphone includes a laser diode and a measuring head, the measuring head can be mounted movably, with the drive of the displacer moving the measuring head relative to the laser diode. In an exemplary embodiment, the measuring head, in addition to being moved back and forth from a sound field or a measuring surface, also scans back and forth across the sound field.

In an exemplary embodiment, the diagnostic system can also include a piezoelectric structure-born sensor or a sound sensor with a diaphragm receiving the sound waves. In this example, the measuring data of the structure-born sensor or of the sound sensor of the diagnostic electronics are transferred, in particular to evaluate the processing of the measuring signal generated by the optical microphone. In this way, the precision of the detection of acoustic operating signals of the actuator can be increased.

In an exemplary embodiment, the optical microphone includes a light source, such as a laser diode, and a measuring head which are coupled through an optical fiber (e.g. flexible optical fiber), such as a fiber optical cable, in such a way that the light source and the measuring head can be kept movable to each other. The measuring head can have at least one beam splitter to generate a first light beam that is exposed to the sound waves of the acoustic operating signal, and a second light beam that at least partially follows a path that is protected against the sound waves.

The disclosure also relates to a diagnostic method or a method for function-monitoring the actuator, such as the control valve, that affects a process medium stream of a process engineering plant, such as a chemical plant, a food processing plant, a power plant or suchlike. According to the disclosure, an acoustic, actuator-specific operating signal, such as operating noises (e.g. leakage sound, cavitation sound) is measured via electromagnetic radiation that is affected by the acoustic, actuator-specific operating signal. Subsequently, an electrical measuring signal that depends on the acoustic, actuator-specific operating signal is generated and provided to diagnostic electronics. During the diagnosis, the measuring signal is compared, in particular with a reference value or a set point, to judge the functionality of the actuator and/or its components.

Furthermore, the disclosure relates to a field device or actuator, such as a control valve, for affecting the process medium stream of the process engineering plant. The actuator can include a diagnostic system. In an exemplary embodiment, the actuator is in addition combined with a pneumatic actuating drive which should operate the actuator.

FIG. 1 illustrates an actuator with a diagnostic system according to an exemplary embodiment of the present disclosure. In an exemplary embodiment, the actuator is extended as a complete field device with the reference number 1 that includes a control valve 3 and a pneumatic actuating drive 5, wherein the control valve housing 7 is carried stationary with the drive housing 11 through a yoke 13.

In an exemplary embodiment, the control valve 3 is integrated into a conduit system of a process engineering plant, wherein the pipe socket is provided with the reference number 15 for the stream input conduit and with reference number 17 for the stream output conduit. A valve seat 21 is stationary fixed to the insight of the control valve housing 7 in the insight of the control valve housing 7. The valve seat 21 cooperates with a valve 23 of the control valve 7 that is operated via a driving rod 25 of the pneumatic actuating drive. The driving rod 25 extends through an opening in the upper part of the control valve housing 7 along the yoke 13 in a passage in the actuating drive housing 11, and is firmly connected with a diaphragm 27 that separates the two working chambers 31, 35 of the pneumatic actuating drive 5.

The actuating drive 5 has one working chamber 31 and a returning chamber 35 that is occupied by a compression spring 33. The pneumatic working chamber 31 is pneumatically connected with a positioner 37 which is connected to a compressed air source 41 of about six bar.

The positioner 37 has a pneumatic output that is coupled via an output conduit 43 with the pneumatic working chamber 31. The positioner 37 includes a position sensor which detects the position of the valve 23 via a scanning arm 45 which is rotatably mounted on the driving rod 25.

In an exemplary embodiment, the diagnostic system of the field device 1 includes an optical microphone 51 that is coupled via a data cable 53 to diagnostic electronics 55 which is arranged in the insight of the housing of the positioner 37. The optical microphone 51 is arranged inside of the yoke 13 and outside of the control valve housing 7 and of the actuating drive housing 11, and is arranged adjacent to the positioner 37. In an exemplary embodiment, the optical microphone 51 can also be arranged inside of the control valve housing 7 and/or of the actuating drive housing 11. In this example, the optical microphone 51 can be exposed either to the process medium that flows through the stream conduit of the process engineering plant, or to the increased air pressure insight of the pneumatic working chamber. The optical microphone 51 has a laser diode whose light is dedicated to a measuring head, in particular to an interferometric mirror. These elements are shown in FIG. 2 in more detail. In an exemplary embodiment, the optical microphone 51 can additionally include a piezoelectric drive element 61 which can displace the laser diode and/or the measuring head relative to the orientation point/sound source (in this case the valve rod) to generate in particular a multidimensional sound field. The drive element 61 can be fed with electric energy via the conduit 53. The conduit 53 can also be designed as optical fiber 67 of the optical microphone 51, wherein one light source 63 is placed in the actuating drive housing, and is optically coupled via the optical fiber 67 with a measuring head 71 of the optical microphone 51.

In an exemplary embodiment, the diagnostic electronics 55 can include a microcomputer that receives and processes (e.g. evaluates) the measuring signals of the optical microphone 51. The microcomputer can be provided with a transmitting device that forwards the diagnosis results or the evaluation results to a control room or a receiver which completes a diagnosis or can display the diagnosis results. The microcomputer in the positioner 37 can be coupled to a memory in which the measuring signals of the optical microphone 51 as well as stored comparison values, in particular empirical values, are stored to set the desired diagnosis. In an exemplary embodiment, the diagnostic electronics 55 includes processor circuitry that is configured to perform one or more operations and/or functions of the diagnostic electronics, such as receiving and storing the electrical measuring signal, process and/or evaluate the received signal, output an alarm signal, influence the closed-loop control of the positioner, and/or forward the electrical measuring signal.

FIG. 2 illustrates the optical microphone 51 according to an exemplary embodiment that can be used for the diagnostic system of the field device 1. In an exemplary embodiment, the optical microphone 51 includes as main components, a light source 63 which can be designed as a laser diode, and a measuring head 71 which can be arranged in the actuating drive housing 11, control valve housing 7, or elsewhere in areas through which the process fluid flows. In an exemplary embodiment, the light beams of the light source 63 are bundled at the input lens 65, which input lens 65 is not necessary for the optical microphone, in order to become concentrated in an optical fiber 67 which for example can be designed as a fiber optical cable. With the use of the optical fiber 67, a greater distance between the light source 63 which has to be positioned secure, and the measuring head which has to be positioned near the sound field can be bridged, wherein the measuring head is generally designated by the reference number 71. In an exemplary embodiment, the measuring head 71 includes a second lens 73 which bundles the light beams leaving the optical fiber 67 and delivers them to a beam splitter 75 at the focal point which beam splitter subdivides the bundled light beams into a first partial beam 77 and into a second partial beam 81. The first partial beam 77 is assigned to a first mirror 83. The second partial beam 81 is assigned to a second mirror 85, wherein both mirrors 83, 85 deflect the respective partial beam 77, 81 to a further beam splitter 87. The further beam splitter 87 combines the partial beams 77, 81 to produce an interference arrangement 91 which interference arrangement becomes assigned via a screen 93 to a photodiode 95 which photodiode 95 emits an electrical measuring signal 97 in accordance with the detected interference intensity.

In an exemplary embodiment, the second beam splitter 87 configured to enable the interference viewing, as well as the second mirror 85, are positioned in a sound protected environment, such as a housing 99, while the first partial beam 77 is exposed to sound waves 101 of the acoustic operating signal. On the basis of the interference 91 of the partial beams 77, 81, it can be determined whether the acoustic operating signal 101 exists and how it is characterized, whereby precise conclusions on functionality/damages of the control valve 3 of the process engineering plant can be made.

CONCLUSION

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, "processor circuitry" can include one or more circuits, one or more processors, logic, or a combination thereof. For example, a circuit can include an analog circuit, a digital circuit, state machine logic, other structural electronic hardware, or a combination thereof. A processor can include a microprocessor, a digital signal processor (DSP), or other hardware processor. In one or more exemplary embodiments, the processor can include a memory, and the processor can be "hard-coded" with instructions to perform corresponding function(s) according to embodiments described herein. In these examples, the hard-coded instructions can be stored on the memory. Alternatively or additionally, the processor can access an internal and/or external memory to retrieve instructions stored in the internal and/or external memory, which when executed by the processor, perform the corresponding function(s) associated with the processor, and/or one or more functions and/or operations related to the operation of a component having the processor included therein.

In one or more of the exemplary embodiments described herein, the memory can be any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST 1 field device
3 control valve
5 actuating drive
7 control valve housing
11 actuating drive housing
13 yoke
15 stream inlet conduit
17 stream outlet conduit
21 valve seat
23 valve
25 driving rod
27 diaphragm
31 working chamber
33 compression spring
35 returning chamber
37 positioner
41 compressed air source
43 output conduit
45 scanning arm
51 optical microphone
53 conduit/cable/optical fiber
55 diagnostic electronics
61 drive element
63 light source
65 input lens
67 optical fiber
71 measuring head
73 lens
75 first beam splitter
77 first partial beam
81 second partial beam
83 first mirror
85 second mirror
87 second beam splitter
91 interference
93 screen
95 photodiode
97 electrical measuring signal
99 housing
101 Sound waves/Sound field

The invention claimed is:

1. A diagnostic system to function-monitor an actuator to affect a process medium stream of a process engineering plant, comprising:
  an optical microphone allocated to the actuator and arranged inside of a housing of the actuator in which the process medium stream flows, the optical microphone being orientated to a valve closer, a valve seat, a valve cage, and/or a valve rod, wherein the optical microphone is configured to:
    measure an acoustic, actuator-specific operating signal, as leakage sound and cavitation sound, based on electromagnetic radiation that is affected by the acoustic, actuator-specific operating signal, and
    generate an electrical measuring signal based on the measured acoustic, actuator-specific operating signal; and
  diagnostic electronics that are configured to receive and store, process, and/or transmit the electrical measuring signal.

2. The diagnostic system according to claim 1, wherein the optical microphone is configured to monitor a change of a refraction index of air in a course of sound waves of the acoustic, actuator-specific operating signal to optically measure sound pressure.

3. The diagnostic system according to claim 1, wherein:
  the optical microphone is arranged in a conduit of the process engineering plant that leads the process medium stream, wherein the optical microphone is orientated to the inside of the housing of the actuator.

4. The diagnostic system according to claim 1, further comprising a piezoelectric structure-borne sound sensor or a sound sensor with a diaphragm, wherein measuring data of the sensor are forwarded to the diagnostic electronics and the diagnostic electronics is configured to evaluate the processing of the electrical measuring signal being generated by the optical microphone.

5. The diagnostic system according to claim 2, wherein the optical microphone comprises a light source including a laser diode, and a measuring head coupled to the light source by an optical fiber cable in such a way that the light source and the measuring head are movable relative to each other, the measuring head including at least one beam splitter configured to create a first light beam that is exposed to the sound waves of the acoustic operating signal, and a second light beam that at least partially follows a path that is protected against the sound waves.

6. The diagnostic system according to claim 1, wherein the actuator is a control valve.

7. The diagnostic system according to claim 1, wherein the process engineering plant is a chemical plant, a food processing plant, or a power plant.

8. An actuator adapted to affect a process medium stream of a process engineering plant comprising:
 a pneumatic actuating drive configured to operate the actuator; and
 the diagnostic system according to claim 1.

9. The diagnostic system according to claim 1, wherein the optical microphone is arranged in a pneumatic conduit of a pneumatic actuating drive system of the actuator, the optical microphone being orientated to a magnetic valve of a positioner of the actuator, and/or the optical microphone being arranged in a pneumatic working chamber of a pneumatic actuating drive of the actuator, the optical microphone being orientated to a diaphragm or a bellow of the actuating drive.

10. The diagnostic system according claim 1, further comprising an adjuster configured to move at least one part of the optical microphone relative to a spatially defined sound field at the actuator.

11. The diagnostic system according to claim 10, wherein the adjuster comprises an electric drive having a piezoelectric material and/or that is fed with electric energy being extracted from the process medium stream or from an auxiliary energy source including a pneumatic pressure source.

12. The diagnostic system according to claim 1, wherein the optical microphone comprises a light source including a laser diode, and a measuring head coupled to the light source by an optical fiber cable such that the light source and the measuring head are movable relative to each other, the measuring head including at least one beam splitter configured to create a first light beam that is exposed to sound waves of the acoustic operating signal, and a second light beam that at least partially follows a path that is protected against the sound waves.

13. The diagnostic system according to claim 1, wherein the optical microphone lacks a diaphragm.

14. A diagnostic system to function-monitor an actuator to affect a process medium stream of a process engineering plant, comprising:
 an optical microphone allocated to the actuator and arranged in a conduit of the process engineering plant that leads the process medium stream, the optical microphone being orientated to an inside of a housing of the actuator, wherein the optical microphone is configured to:
  measure an acoustic, actuator-specific operating signal, as leakage sound and cavitation sound, based on electromagnetic radiation that is affected by the acoustic, actuator-specific operating signal, and
  generate an electrical measuring signal based on the measured acoustic, actuator-specific operating signal; and
 diagnostic electronics that are configured to receive and store, process, and/or transmit the electrical measuring signal.

15. A diagnostic system to function-monitor an actuator to affect a process medium stream of a process engineering plant, comprising:
 an optical microphone allocated to the actuator and configured to:
  measure an acoustic, actuator-specific operating signal, as leakage sound and cavitation sound, based on electromagnetic radiation that is affected by the acoustic, actuator-specific operating signal, and
  generate an electrical measuring signal based on the measured acoustic, actuator-specific operating signal; and
 diagnostic electronics that are configured to receive and store, process, and/or transmit the electrical measuring signal, wherein the optical microphone includes an arrangement of at least two optical sub-microphones configured to generate respective measuring signals to conduct a three-dimensional resolution of a sound field of the acoustic, actuator-specific operating signal, the arrangement of at least two sub-microphones being configured to perform the three dimensional resolution of the sound field in such a way that the arrangement localizes a sound source and/or determines the sound velocity.

16. The diagnostic system according to claim 15, wherein the sound source is of a leakage or a cavitation.

* * * * *